United States Patent
Ishiwata et al.

(10) Patent No.: US 10,026,999 B2
(45) Date of Patent: Jul. 17, 2018

(54) DETECTION METHOD AND DETECTION DEVICE

(71) Applicant: Nissan Motor Co., Ltd., Yokohama-shi, Kanagawa (JP)

(72) Inventors: Teruyuki Ishiwata, Kanagawa (JP); Isao Aramaki, Kanagawa (JP)

(73) Assignee: Nissan Motor Co., Ltd., Yokohama (JP)

( * ) Notice: Subject to any disclaimer, the term of this patent is extended or adjusted under 35 U.S.C. 154(b) by 0 days.

(21) Appl. No.: 15/039,488

(22) PCT Filed: Oct. 28, 2014

(86) PCT No.: PCT/JP2014/078658
§ 371 (c)(1),
(2) Date: May 26, 2016

(87) PCT Pub. No.: WO2015/087631
PCT Pub. Date: Jun. 18, 2015

(65) Prior Publication Data
US 2017/0214101 A1 Jul. 27, 2017

(30) Foreign Application Priority Data
Dec. 10, 2013 (JP) ................................ 2013-255449

(51) Int. Cl.
*H01M 10/48* (2006.01)
*H01M 2/18* (2006.01)
(Continued)

(52) U.S. Cl.
CPC ............ *H01M 10/48* (2013.01); *G01N 21/88* (2013.01); *G01N 21/95* (2013.01); *H01M 2/1673* (2013.01); *H01M 2/18* (2013.01)

(58) Field of Classification Search
CPC .................................................. H01M 10/48
(Continued)

(56) References Cited

U.S. PATENT DOCUMENTS

2007/0049155 A1* 3/2007 Moro .................... H01L 51/448
445/24
2012/0148880 A1* 6/2012 Schaefer ............... H01M 10/48
429/50
(Continued)

FOREIGN PATENT DOCUMENTS

JP 3380935 B2 12/2002
JP 2003-344020 A 12/2003
(Continued)

*Primary Examiner* — Tarifur Chowdhury
*Assistant Examiner* — Omar Nixon
(74) *Attorney, Agent, or Firm* — Global IP Counselors, LLP

(57) ABSTRACT

A detection method in which light is irradiated on a bagged electrode, and an electrode is disposed inside of a bag-shaped separator for detecting breakage of the separator, the method includes capturing an image by irradiating the light onto the bagged electrode so that a first portion in which the light has been transmitted through n layers of the separator, and a second portion in which the light has been transmitted through equal to or less than n−1 layers of the separator, will have mutually different brightness levels, while capturing an image of the bagged electrode, detecting the first portion from the brightness of the image that is obtained by capturing the bagged electrode, and determining a breakage of the separator, based on the distance between edges of the first portion, and of an electrode portion where the light does not pass through.

11 Claims, 16 Drawing Sheets

(51) Int. Cl.
      *G01N 21/88*   (2006.01)
      *G01N 21/95*   (2006.01)
      *H01M 2/16*    (2006.01)

(58) Field of Classification Search
      USPC .................................................. 356/239.3
      See application file for complete search history.

(56) References Cited

U.S. PATENT DOCUMENTS

| | | | |
|---|---|---|---|
| 2012/0300158 A1* | 11/2012 | Chae | G02F 1/1343 |
| | | | 349/106 |
| 2014/0020235 A1 | 1/2014 | Aramaki et al. | |
| 2014/0026398 A1 | 1/2014 | Watanabe et al. | |
| 2014/0185058 A1 | 7/2014 | Hirayama et al. | |

FOREIGN PATENT DOCUMENTS

| | | | |
|---|---|---|---|
| JP | 2007-265863 A | 10/2007 |
| WO | 2012/137594 A1 | 10/2012 |
| WO | 2012/137917 A1 | 10/2012 |
| WO | 2012/137926 A1 | 10/2012 |

\* cited by examiner

DETECTION METHOD AND DETECTION DEVICE

CROSS-REFERENCE TO RELATED APPLICATIONS

This application is a U.S. National Stage Application of International Application No. PCT/JP2014/078658, filed Oct. 28, 2014, which claims priority to Japanese Application No. 2013-255449, filed Dec. 10, 2013, the contents of each of which are hereby incorporated herein by reference.

BACKGROUND

Field of Invention

The present invention relates to a detection method and a detection device for breakage of a separator.

Background Information

In recent years, secondary batteries have been used in various products. Secondary batteries include a battery element in which a positive electrode, a separator, and a negative electrode are layered. In a battery element, layering without a misalignment is important to prevent deterioration in the battery performance and battery life.

A technique to quickly and accurately layer a positive electrode and a negative electrode by disposing a positive electrode inside a bag-shaped separator, and layering a negative electrode and the bag-like separator in which the positive electrode is disposed (referred to as a bagged electrode) has been disclosed (refer to Japanese Patent No. 3380935).

However, in the layering method disclosed in Japanese Patent No. 3380935, there is the possibility that the separator is curled when transporting the bagged electrode, and the separator is layered in a broken state. Therefore, a method is required for detecting curling and breakage of separators in bagged electrodes.

SUMMARY

A method to irradiate light on a bagged electrode from above and capturing an image of the bagged electrode by an image capturing unit provided above can be conceived as a method to detect curling and breakage of a separator. However, with this method, while breakage of a separator disposed on the image capturing unit side, that is, on the upper side of the bagged electrode, can be discovered, breakage of a separator disposed on the opposite side of the image capturing unit, that is, on the lower side of the bagged electrode, cannot be detected. In this case, there are cases in which a battery element has breakage and curling of the separator remaining, posing issues in the battery performance.

In view of the above circumstances, an object of the present invention is to provide a detection method and a detection device that can detect breakage of a separator regardless of the position of the separator, with respect to a bagged electrode, wherein an electrode is disposed inside of a bag-shaped separator.

The detection method according to the present invention which achieves the object above is a detection method in which light is irradiated on a bagged electrode, wherein an electrode is disposed inside of a bag-shaped separator, to detect a breakage of the separator. The detection method comprises an image capturing step for irradiating the light to the bagged electrode so that a first portion in which the light has been transmitted through n-layers of separators, and a second portion in which the light has been transmitted through equal to or less than n−1 layers of separators, will have mutually different brightness levels, while capturing an image of the bagged electrode. The detection method further comprises a detection step in which the first portion is detected from the brightness of the image that is obtained by capturing the bagged electrode in the image capturing step. The detection method further comprises a determination step for determining a breakage of the separator, based on the distance between edges of the first portion which is detected in the detection step, and of the electrode portion where the light does not pass through.

The detection device according to the present invention which achieves the object above is a detection device in which light is irradiated on a bagged electrode, wherein an electrode is disposed inside of a bag-shaped separator, to detect breakage of the separator. The detection device comprises an image capturing device for irradiating the light to the bagged electrode by an irradiation device so that a first portion in which the light has been transmitted through n-layers of separators, and a second portion in which the light has been transmitted through equal to or less than n−1 layers of separators, will have mutually different brightness levels, while capturing an image of the bagged electrode. The detection device further comprises a detection device that detects the first portion from the brightness of the image that is obtained by capturing the bagged electrode by the image capturing device. The detection device further comprises a determination device for determining a breakage of the separator, based on the distance between edges of the first portion which is detected by the detection means, and of the electrode portion where the light does not pass through.

According to the detection method and the detection device described above, it is possible to distinguish between a portion where the number of separators is n sheets and a portion where the number of separators is n−1 sheets. Therefore, breakage of a separator can be detected regardless of the position of the separator, with respect to a bagged electrode, wherein an electrode is disposed inside of a bag-shaped separator.

BRIEF DESCRIPTION OF THE DRAWINGS

Referring now to the attached drawings which form a part of this original disclosure.

DETAILED DESCRIPTION OF THE EMBODIMENTS

First Embodiment

Figure 1:
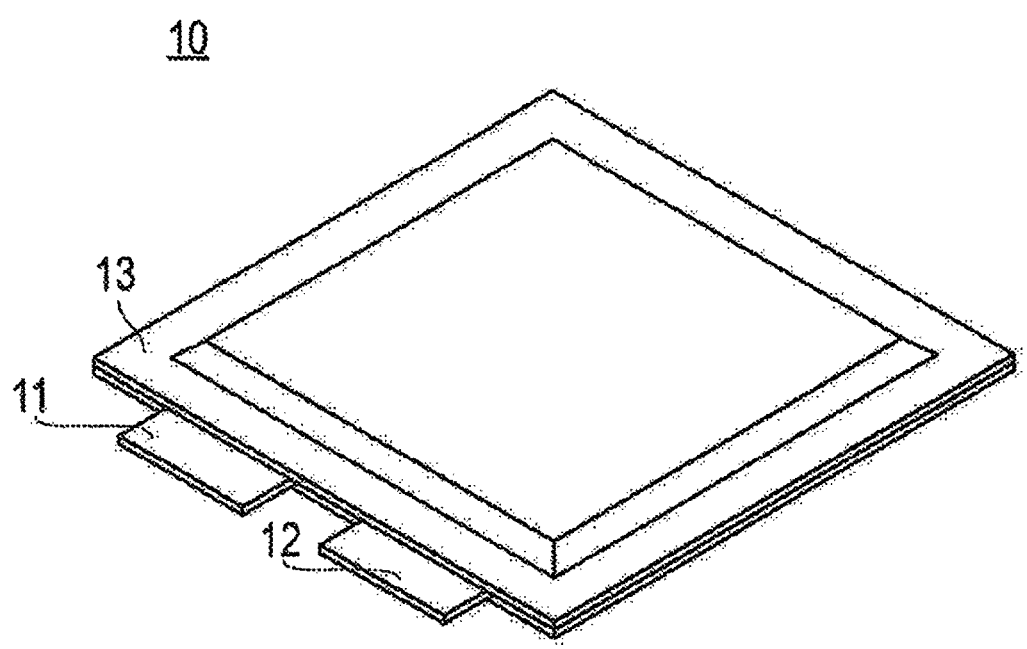
FIG. 1 is a perspective view representing an appearance of a lithium ion secondary battery.

Embodiments of the present invention will be described below, with reference to the appended drawings. The dimensional ratios in the drawings are exaggerated for convenience of explanation, and may be different from the actual ratios.

The present invention relates to a detection method and a detection device which are applied to a part of the manufacturing process of a lithium ion secondary battery. Before describing the detection method and the detection device which are one embodiment of the present invention, the structure of a lithium ion secondary battery, and a sheet laminating device, which is a structure for assembling the power generating element of a lithium ion secondary battery will be described.

Lithium Ion Secondary Battery

Figure 2:
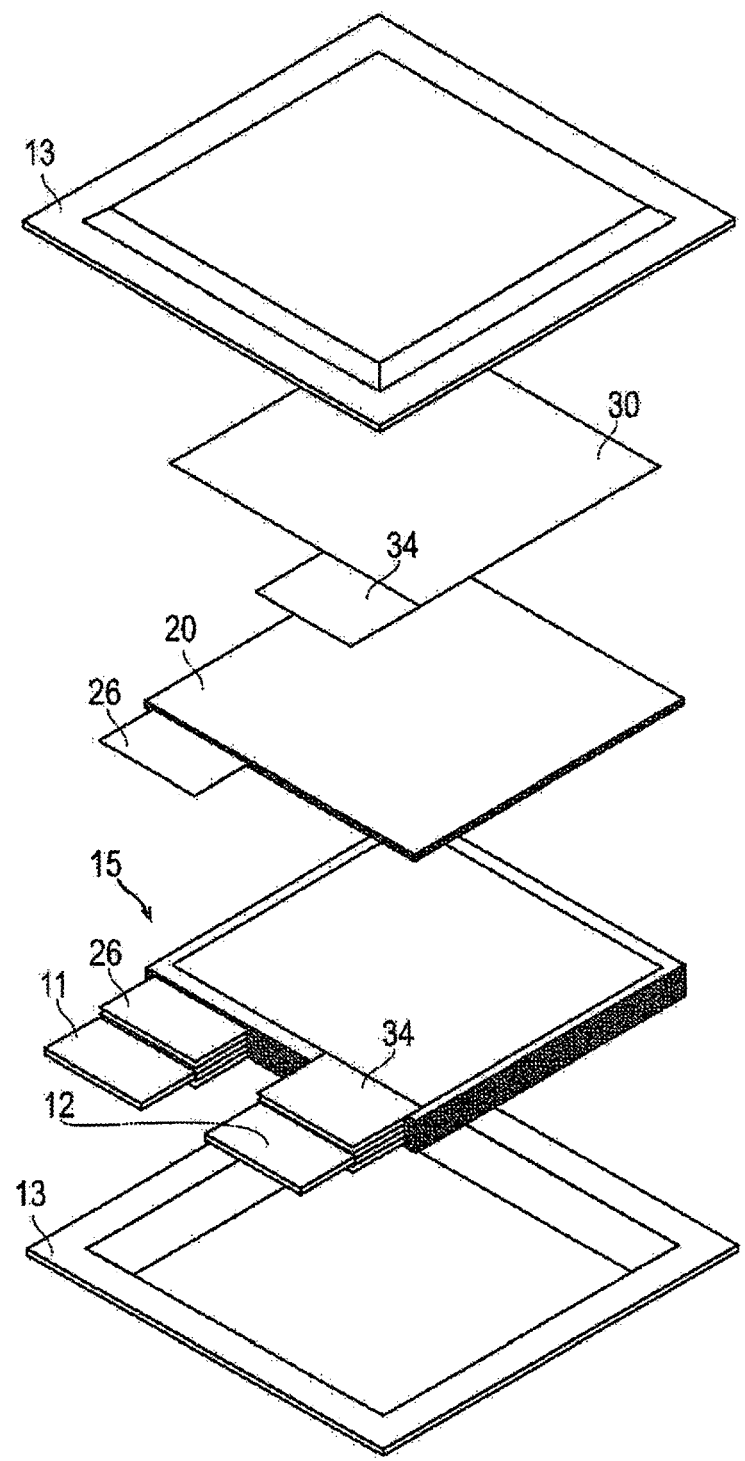
FIG. 2 is an exploded perspective view of the lithium ion secondary battery.

First, a lithium ion secondary battery 10 formed by a sheet laminating device 100 will be described, with reference to FIG. 1-FIG. 4. FIG. 1 is a perspective view representing the appearance of the lithium ion secondary battery 10. FIG. 2 is an exploded perspective view of the lithium ion secondary battery 10. FIG. 3 is a plan view of a bagged positive electrode 20 and a negative electrode 30. FIG. 4 is a plan view illustrating a state in which the negative electrode 30 is superposed on the bagged positive electrode 20.

The lithium ion secondary battery 10 has a flat rectangular shape, and a positive electrode lead 11 and a negative electrode lead 12 are led from the same end of an exterior material 13, as illustrated in FIG. 1. The configuration is not limited thereto, and the positive electrode lead 11 and the negative electrode lead 12 may be led from mutually different ends. A power generating element 15 in which a charge/discharge reaction proceeds is housed inside the exterior material 13. The power generating element 15 is formed by a bagged positive electrode 20 and a negative electrode 30 being alternately laminated, as illustrated in FIG. 2.

Figure 3A:
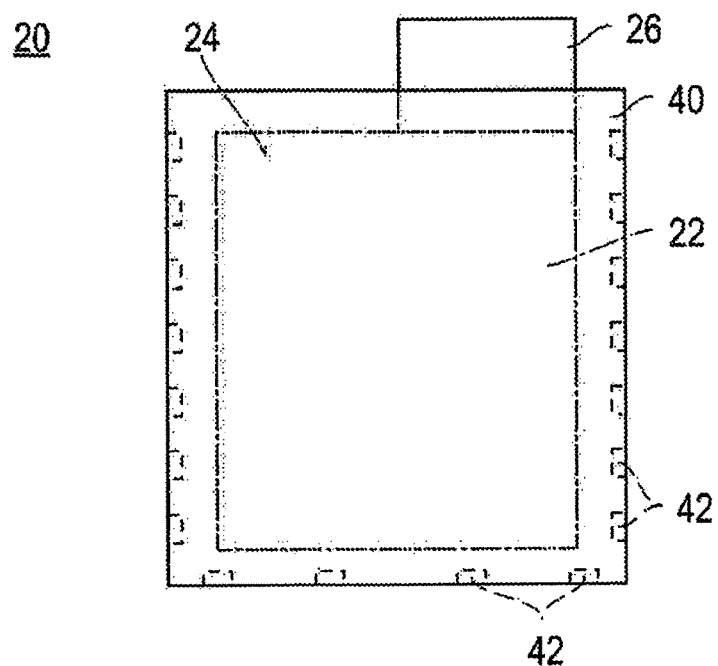
FIGS. 3A-3B are plan views of a bagged positive electrode and a negative electrode.
Figure 4:
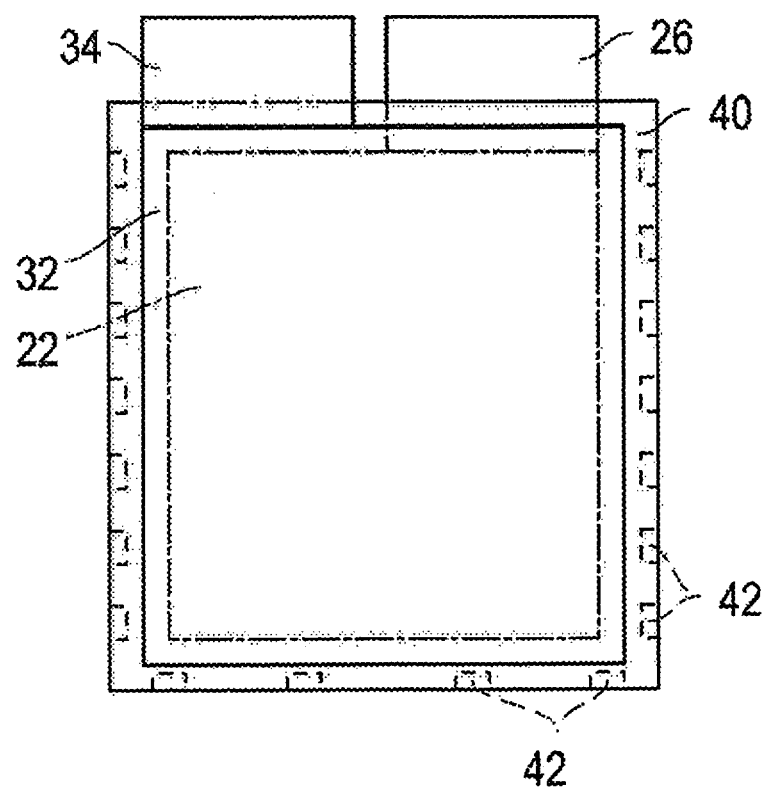
FIG. 4 is a plan view illustrating a state in which a negative electrode is superposed on a bagged positive electrode.

The bagged positive electrode 20 is formed by a positive electrode 24, made by positive electrode active material layers 22 being formed on both surfaces of a sheet-like positive electrode current collector, being sandwiched by separators 40, as illustrated in FIG. 3A. The two separators 40 are bonded to each other at the ends by a bonding portion 42 and formed in the shape of a bag. A tab portion 26 of the positive electrode 24 is drawn out from the separator 40 bag. Positive electrode active material layers 22 are formed on the positive electrode 24 in the portion other than the tab portion 26.

Figure 3B:
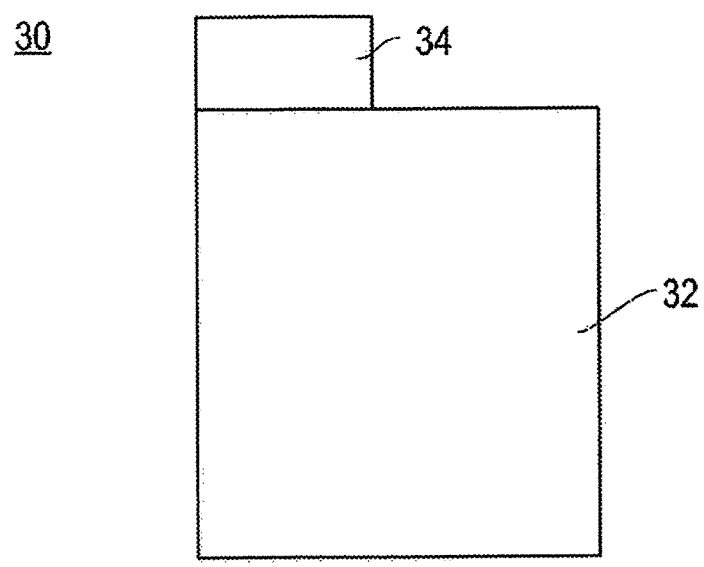

The negative electrode 30 is made by negative electrode active material layers 32 being formed on both surfaces of an extremely thin sheet-like negative electrode current collector, as illustrated in FIG. 3B. Negative electrode active material layers 32 are formed on the negative electrode 30 in the portion other than a tab portion 34.

The material that configures the separator 40 may be, for example, a polyolefin porous membrane, such as polyethylene and polypropylene. Not limited thereto, the separator 40 may be a ceramic separator as well.

A state in which the negative electrode 30 is superposed on the bagged positive electrode 20 is illustrated in FIG. 4. The negative electrode active material layer 32 is formed to be slightly larger than the positive electrode active material layer 22 of the positive electrode 24 in plan view, as illustrated in FIG. 4.

The method itself for producing a lithium ion secondary battery 10 by alternately laminating a bagged positive electrode 20 and a negative electrode 30 is a common manufacturing method of a lithium ion secondary battery 10, and thus a detailed description thereof will be omitted.

Sheet Laminating Device

Next, the sheet laminating device 100 for assembling a power generating element 15 will be described.

Figure 5:
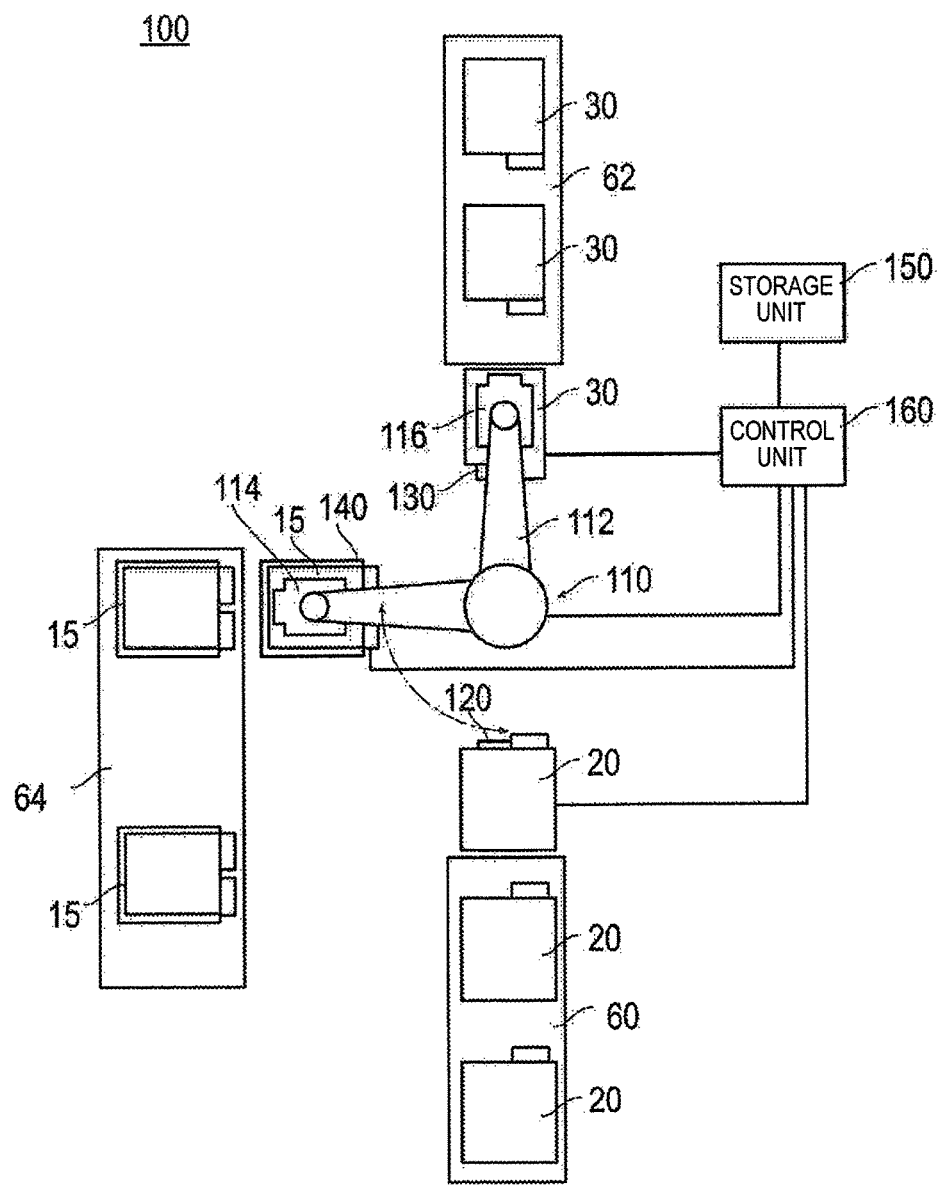
FIG. 5 is a schematic plan view illustrating a sheet laminating device.
Figure 6:
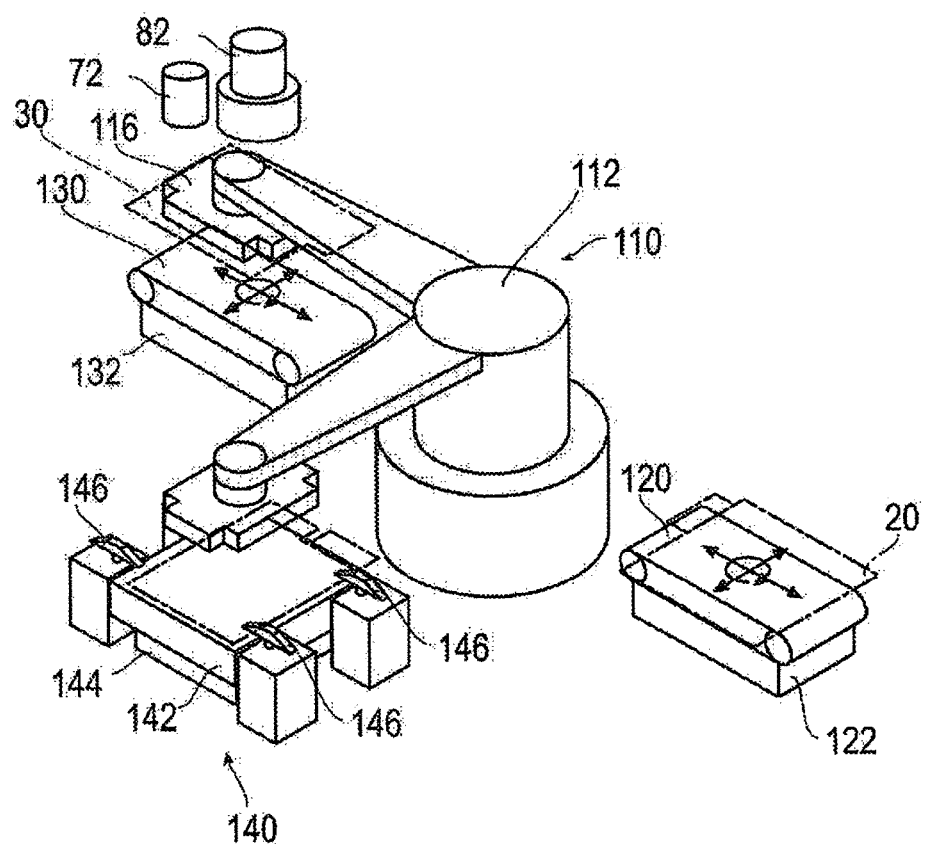
FIG. 6 is a schematic perspective view illustrating the sheet laminating device.
Figure 7:
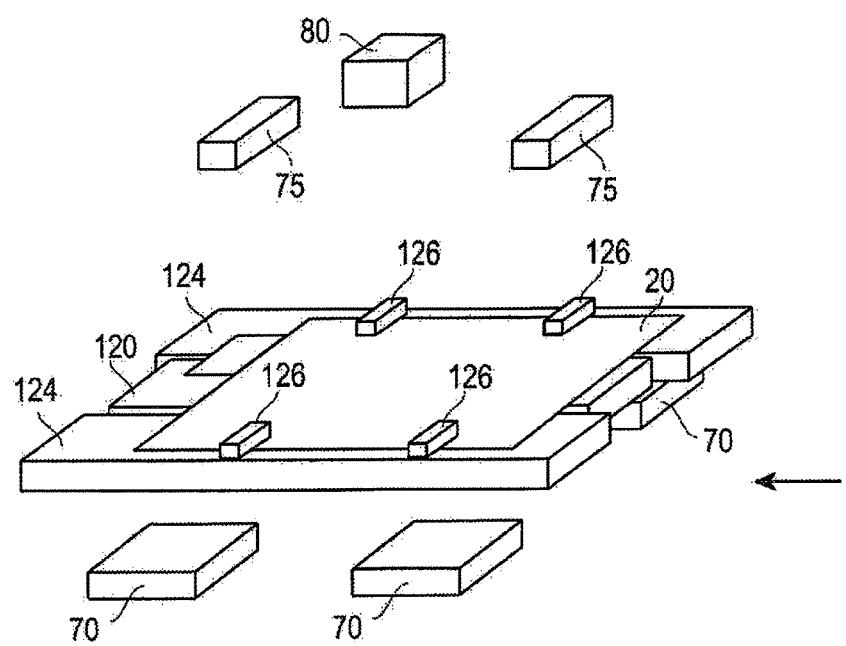
FIG. 7 is a perspective view illustrating an inspection system.
Figure 8:
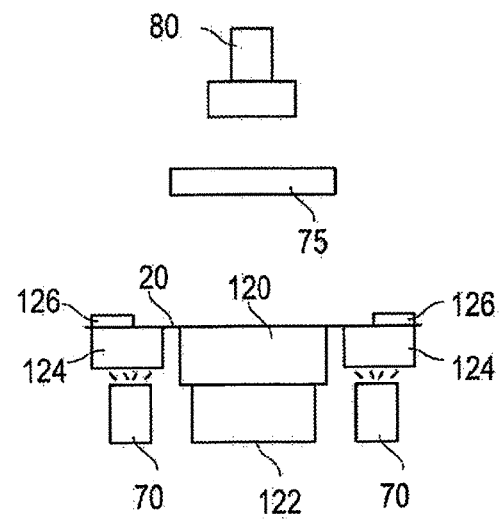
FIG. 8 is a view illustrating the inspection system viewed from the direction of the arrow in FIG. 7.

FIG. 5 is a schematic plan view illustrating the sheet laminating device 100. FIG. 6 is a schematic perspective view illustrating the sheet laminating device 100. FIG. 7 is a perspective view illustrating an inspection system 200. FIG. 8 is a view illustrating the inspection system 200 viewed from the direction of the arrow in FIG. 7.

The sheet laminating device 100 comprises a laminating robot 110, a positive electrode supply table 120, a negative electrode supply table 130, a lamination stage 140, a storage unit 150, and a control unit 160, as illustrated in FIG. 5 and FIG. 6. The laminating robot 110, the positive electrode supply table 120, the negative electrode supply table 130, and the lamination stage 140 are controlled by the control unit 160. The control program and various data of the control unit 160 are stored in the storage unit 150.

The laminating robot 110 forms a power generating element 15 by alternately laminating a bagged positive electrode 20 and a negative electrode 30. The laminating robot 110 comprises an L-shaped arm 112, and first and second suction hands 114, 116 provided at the ends of the L-shaped arm 112. The L-shaped arm 112 is turned about a vertical axis by a predetermined angle, for example, by 90 degrees in the present embodiment. The L-shaped arm 112 may be moved in the vertical direction by a predetermined amount. The first suction hand 114 is provided to one end of the L-shaped arm 112, and holds and releases the bagged positive electrode 20 by suction. The second suction hand 116 is provided to the other end of the L-shaped arm 112, and holds and releases the negative electrode 30 by suction.

The positive electrode supply table 120 is a table for handing off the bagged positive electrode 20 to the L-shaped arm 112. The positive electrode supply table 120 receives, and places thereon, bagged positive electrodes 20 which are prepared in the previous step and conveyed by a suction conveyor 60 one by one. Specifically, the positive electrode supply table 120 is also a suction conveyor, which suctions a bagged positive electrode 20 from the suction conveyor 60, the negative pressure of which has been released, carries the same substantially to the center, and fixes the same by negative pressure. When a bagged positive electrode 20 is suctioned by the first suction hand 114, the positive electrode supply table 120 releases the suction thereof. The positive electrode supply table 120 is capable of moving in the planar direction, as well as rotating about a vertical axis, so as to be capable of adjusting the planar position of the bagged positive electrode 20. The positive electrode supply table 120 is provided on an XY stage 122, and the planar position of the bagged positive electrode 20 is adjusted by the XY stage 122 moving in the X and Y directions, or by being rotated about a vertical axis, as illustrated in FIG. 6. The movement of the XY stage 122 in the planar direction, as well as the rotation thereof about a vertical axis, are realized by three motors (not shown).

The positive electrode supply table 120 is configured to have a narrower width than the suction conveyor 60 so that the lateral side of the bagged positive electrode 20 will protrude therefrom. On the other hand, while not shown in FIGS. 5, 6, a transparent supporting platform 124 for supporting the ends of the bagged positive electrode 20 that protrude from the positive electrode supply table 120 is provided on the peripheral edge of the positive electrode supply table 120, as illustrated in FIGS. 7, 8. A clamper 126 is provided in a position corresponding to the supporting platform 124. The clamper 126 sandwiches and fixes the ends of the bagged positive electrode 20 along with the supporting platform 124. The supporting platform 124 and the clamper 126 are both movable, and approach the bagged positive electrode 20 when a bagged positive electrode 20 is placed on the positive electrode supply table 120 so as to support and fix the ends of the bagged positive electrode 20.

The position of the positive electrode 24 of the bagged positive electrode 20 which is disposed on the positive electrode supply table 120 is detected by an inspection system 200 described later. Then, the horizontal position of the positive electrode 24 (bagged positive electrode 20) is corrected based on the position of the positive electrode 24 detected by the inspection system 200. With this correction, the first suction hand 114 is able to pick-up a bagged positive electrode 20 every time, in which the position of the positive electrode 24 has been accurately positioned.

The negative electrode supply table 130 is a table for handing off the negative electrode 30 to the L-shaped arm 112, as illustrated in FIG. 5 and FIG. 6. The negative electrode supply table 130 receives, and places thereon, negative electrodes 30 which are prepared in the previous step and conveyed by a suction conveyor 62 one by one. Specifically, the negative electrode supply table 130 is also a suction conveyor, which suctions a negative electrode 30 from the suction conveyor 62, the negative pressure of which has been released, carries the same substantially to the center, and fixes the same by negative pressure. When a negative electrode 30 is suctioned by the second suction hand 116, the negative electrode supply table 130 releases the suction thereof. In addition, the negative electrode supply table 130 is capable of moving in the planar direction, as well as rotating about a vertical axis, so as to be capable of adjusting the planar position of the negative electrode 30. The negative electrode supply table 130 is provided on an XY stage 132, and the planar position of the negative electrode 30 is adjusted by the XY stage 132 moving in the X and Y directions, or by being rotated about a vertical axis, as illustrated in FIG. 6. The movement of the XY stage 132 in the planar direction, as well as the rotation thereof about a vertical axis, is realized by three motors (not shown).

In addition, a light source 72 and a camera 82 are disposed above the negative electrode supply table 130, as illustrated in FIG. 6. The light source 72 irradiates, to the negative electrode 30, light having a wavelength that is reflected or absorbed by the negative electrode 30. The camera 82 receives the light that is thrown from the light source 72 and reflected by the negative electrode 30, or, receives the light that is not absorbed by the negative electrode 30 and reflected to the surrounding, to capture the position of the negative electrode 30. In the negative electrode supply table 130, the horizontal position of the negative electrode 30 is corrected based on the position of the negative electrode 30 that is captured by the camera 82. With this correction, the second suction hand 116 is able to pick-up an accurately positioned negative electrode every time.

The lamination stage 140 comprises a placing part 142 on which is placed a laminated body made by alternately laminating a bagged positive electrode 20 and a negative electrode 30, a driving unit 144 for raising and lowering the placing part 142, and four clampers 146 which are disposed on the peripheral portion of the placing part 142.

The placing part 142 holds the laminated body until a predetermined number of sheets of the bagged positive electrodes 20 and the negative electrodes 30 are laminated to complete a power generating element 15 and, when completed, sends out the power generating element 15 to the conveyor 64, as illustrated in FIG. 5. The driving unit 144 adjusts the height of the placing part 142. Specifically, even if bagged positive electrodes 20 and negative electrodes 30 are alternately laminated and the height of the laminated body is varied, the driving unit lowers the position of the placing part 142 according to the progress of the lamination so that the height of the uppermost surface of the laminated body will not change. Accordingly, the laminating robot 110 is capable of laminating bagged positive electrodes 20 and negative electrodes 30 by repeating the same operation, regardless of the progress of the lamination. The clamper 146 fixes the peripheral portion of the laminated body each time a negative electrode 30 or a bagged positive electrode 20 is laminated so that the laminated body will not shift. Since the height of the placing part 142 is adjusted according to the progress of lamination, the clamper 146 can repeatedly carry out clamping with the same motion every time.

Lamination Operation

Using a sheet laminating device 100 configured as described above, bagged positive electrodes 20 and negative electrodes 30 which are subjected to positional adjustment and placed on the positive electrode supply table 120 and the negative electrode supply table 130 are picked up by the laminating robot 110 and alternately provided to the lamination stage 140. The lamination operation of the sheet laminating device 100 will be described below, with reference to FIG. 9-FIG. 11.

FIG. 9A-FIG. 11 are views for explaining the layering operation of the negative electrode and the bagged positive electrode by a laminating robot. In FIG. 9A thru FIG. 11, the XY stages 112, 132 are omitted for ease of understanding. The operation of the laminating robot 110 layering the bagged positive electrode 20 on the lamination stage 140 will be described below.

Figure 9A:
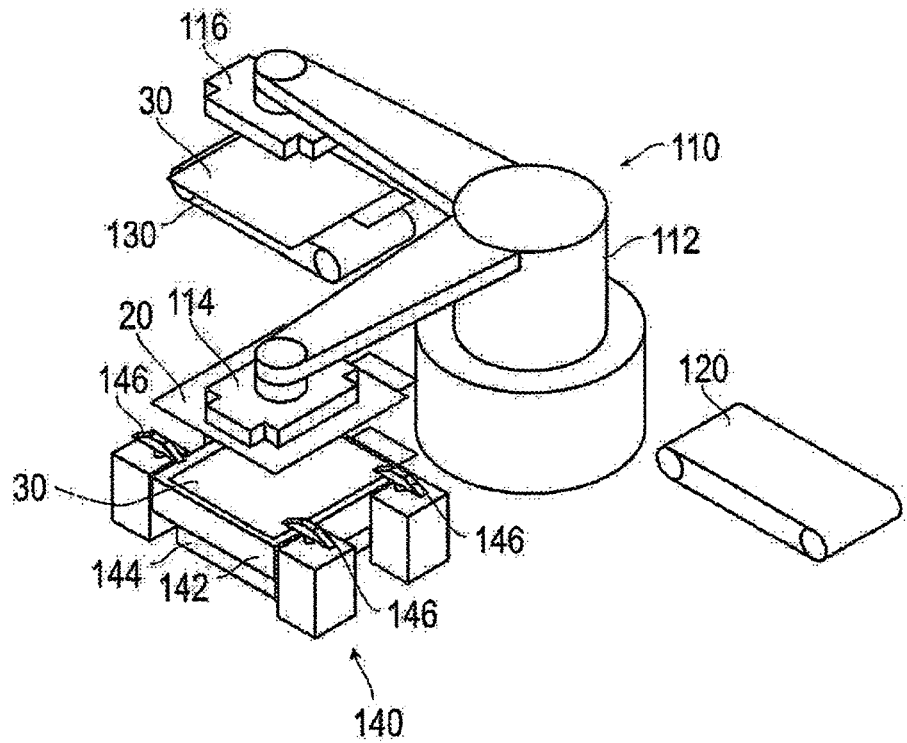
FIGS. 9A-9B are views for explaining the layering operation of the negative electrode and the bagged positive electrode by a laminating robot.

Bagged positive electrodes 20 and negative electrodes 30 are layered on the lamination stage 140, and the first suction hand 114 is positioned above the lamination stage 140, as illustrated in FIG. 9A. A negative electrode 30 is disposed on the uppermost layer of the laminated body of bagged positive electrodes 20 and negative electrodes 30, and the first suction hand 114 is suction holding a bagged positive electrode 20. On the other hand, the second suction hand 116 is positioned above the negative electrode supply table 130. A negative electrode 30 is placed on the negative electrode supply table 130.

Figure 9B:
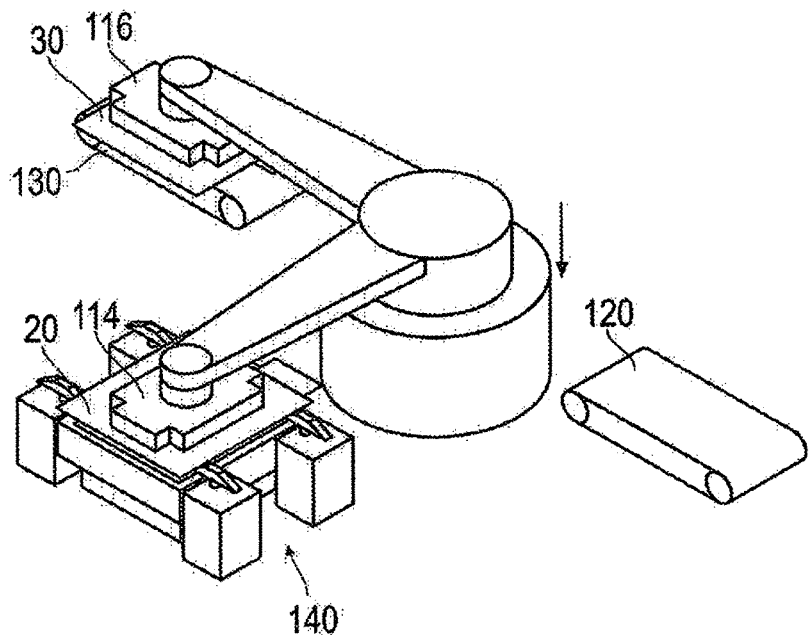

Subsequently, the L-shaped arm 112 of the laminating robot 110 is lowered by a predetermined amount (refer to FIG. 9B arrow). The first suction hand 114 and the second suction hand 116 are each lowered to the lamination stage 140 and the negative electrode supply table 130, accompanying the lowering of the L-shaped arm 112. Negative pressure acts on the bottom surface of the second suction hand 116 at this time, and the second suction hand 116 suction holds the negative electrode 30. On the other hand, the negative pressure of the first suction hand 114 is released, releasing the bagged positive electrode 20.

Figure 10A:
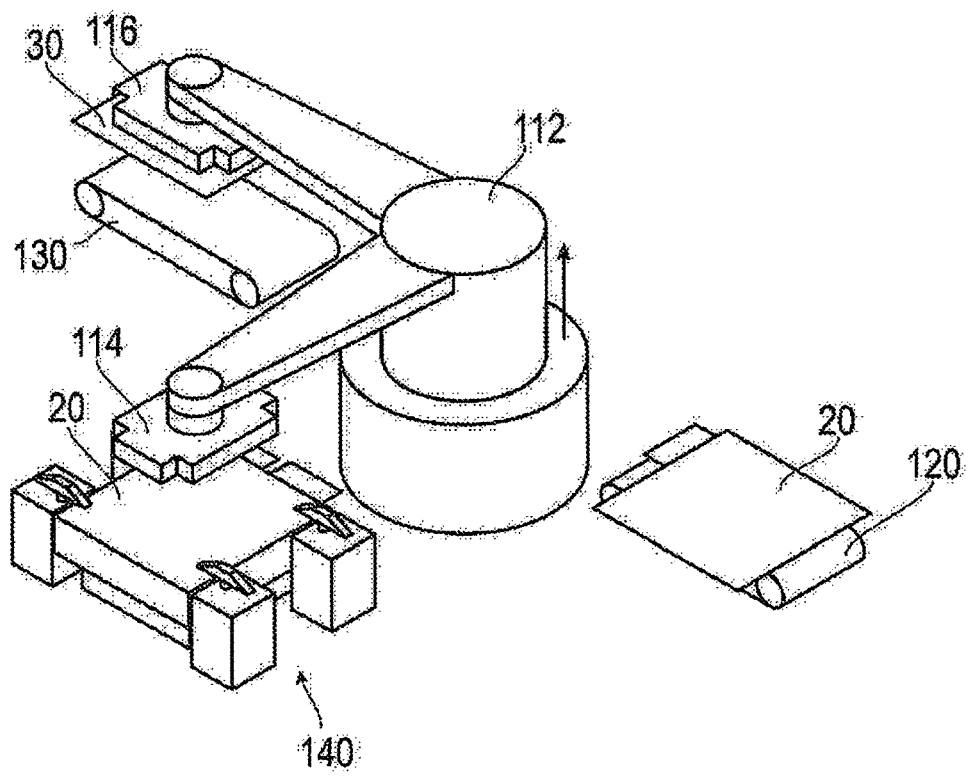
FIGS. 10A-10B are views for explaining the layering operation of the negative electrode and the bagged positive electrode by a laminating robot.

Next, the L-shaped arm 112 of the laminating robot 110 is raised by a predetermined amount (refer to FIG. 10A arrow). The second suction hand 116 picks up the negative electrode 30 from the table 130 accompanying the rise of the L-shaped arm 112. In addition, the first suction hand 114 and the second suction hand 116 are each moved above the lamination stage 140 and the negative electrode supply table 130, respectively.

Figure 10B:
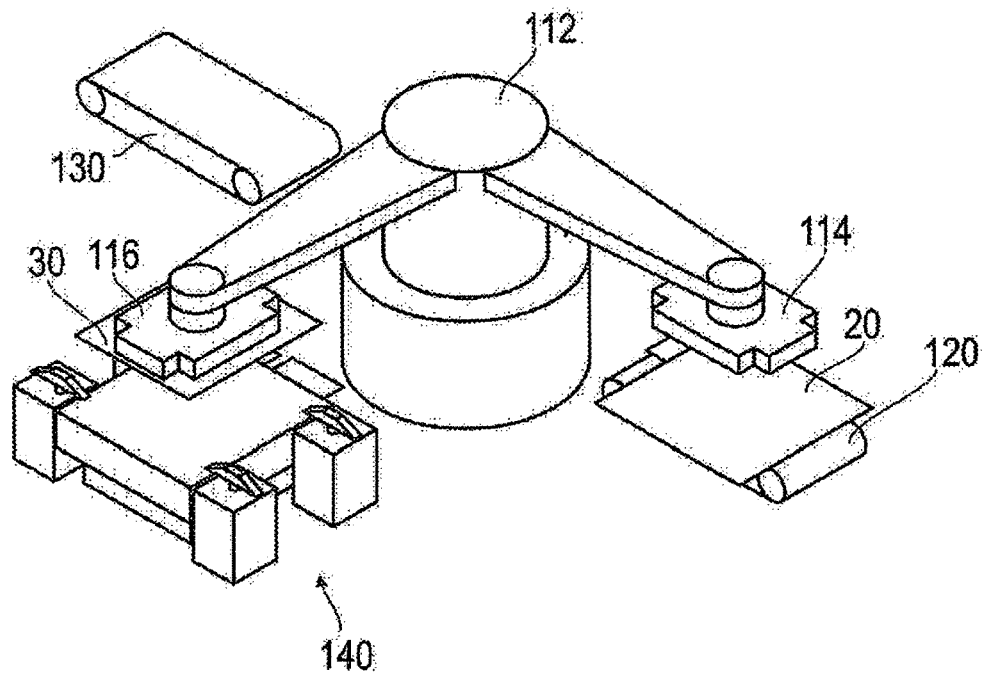

Next, the L-shaped arm 112 of the laminating robot 110 is turned by a predetermined amount (refer to FIG. 10B). Specifically, the first suction hand 114 will be positioned above the positive electrode supply table 120 and the second suction hand 116 will be positioned above the lamination stage 140, by the L-shaped arm 112 being turned 90 degrees about a vertical axis.

Figure 11A:
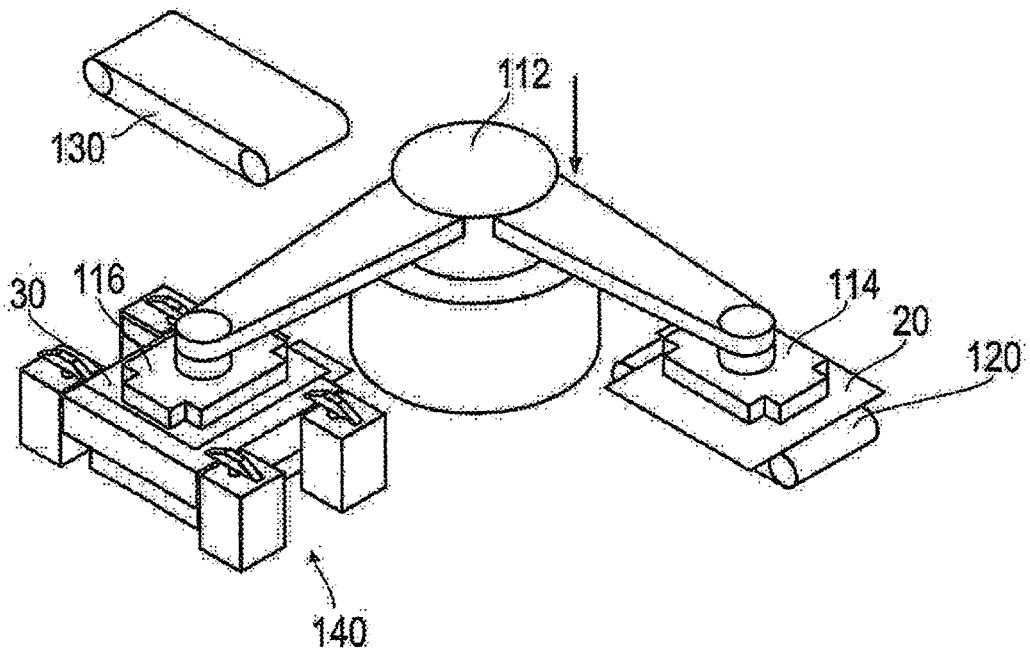
FIGS. 11A-11B are view for explaining the layering operation of the negative electrode and the bagged positive electrode by a laminating robot.

Subsequently, the L-shaped arm 112 of the laminating robot 110 is lowered by a predetermined amount (refer to FIG. 11A arrow). The first suction hand 114 and the second suction hand 116 each reach above the positive electrode supply table 120 and the lamination stage 140, accompanying the lowering of the L-shaped arm 112. Negative pressure acts on the bottom surface of the first suction hand 114 at this time, and the first suction hand 114 suction holds the bagged positive electrode 20 on the table 120. On the other hand, the negative pressure of the second suction hand 116 is released, and the second suction hand 116 releases the negative electrode 30 on the uppermost surface of the laminated body on the lamination stage 140.

Figure 11B:
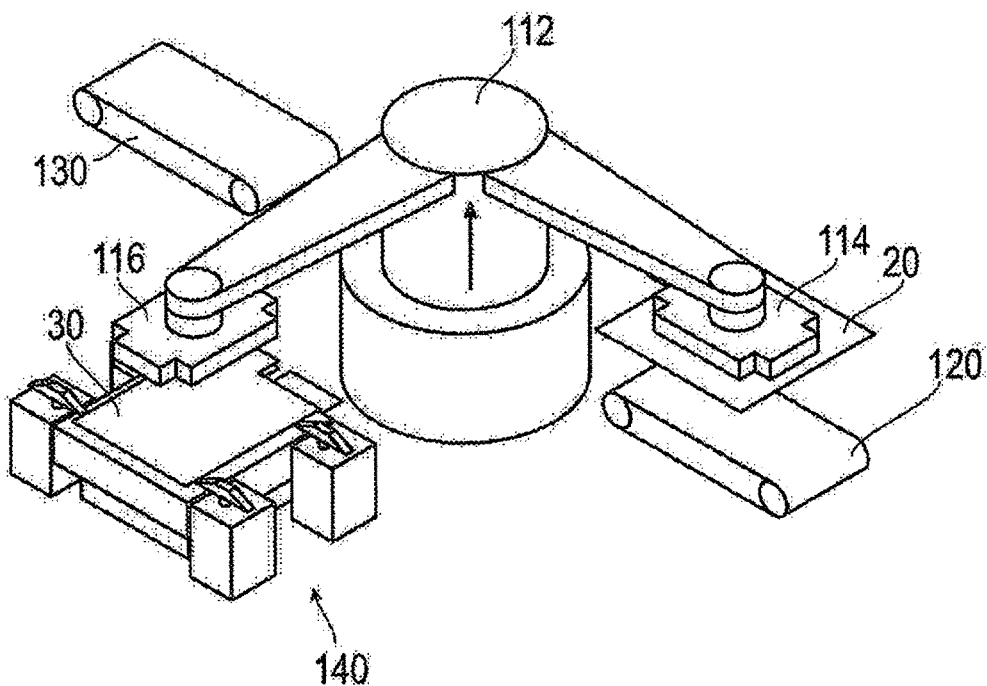

Next, the L-shaped arm 112 of the laminating robot 110 is raised by a predetermined amount (refer to FIG. 11B arrow). The first suction hand 114 picks up the bagged positive electrode 20 from the positive electrode supply table 120 accompanying the rise of the L-shaped arm 112. On the other hand, the second suction hand 116 is moved above the lamination stage 140.

Next, the L-shaped arm 112 of the laminating robot 110 is turned by a predetermined amount. The first suction hand 114 will be positioned above the lamination stage 140 and the second suction hand 116 will be positioned above the table 130, by the L-shaped arm 112 being turned −90 degrees about a vertical axis (refer to FIG. 9A).

Bagged positive electrodes 20 and negative electrodes 30 are alternately laminated on the lamination stage 140 by the operation above being repeated. A power generating element 15 is formed by a predetermined number of sheets of the bagged positive electrode 20 and the negative electrode 30 being laminated.

Inspection System

The inspection system 200 that is applied to the sheet laminating device 100 above will be described next.

As described above, the inspection system 200 corrects the horizontal position of the bagged positive electrode 20 after detecting the position of the positive electrode 24 inside the bagged positive electrode 20. In addition, the inspection system 200 detects a breakage in the separator 40, which configures the bagged positive electrode 20, as a detection device. Additionally, the inspection system 200 inspects the position of the separator 40. The configuration of the inspection system 200 will be described below, with reference to FIG. 7 again. In FIG. 7, an illustration of the control unit 160 is omitted.

The inspection system 200 comprises a transmissive light source (irradiation device) 70, a reflected light source 75, a camera (image capturing device) 80, and a control unit 160. The transmissive light source 70, the reflected light source 75, and the camera 80 are connected to the control unit 160, and the operations thereof are controlled by the control unit 160.

Four transmissive light sources 70 are arranged below the positive electrode supply table 120, which irradiate light to the bagged positive electrode 20 from below. The intensity of light of the transmissive light source 70 can be adjusted by an adjustment dial (not shown). The wavelength of the light that is irradiated from the transmissive light source 70 is preferably a wavelength that is transmitted through the separator 40 but is not transmitted through the positive electrode 24, for example, red light.

The reflected light source 75 is arranged above the positive electrode supply table 120 and irradiates light to the bagged positive electrode 20. The reflected light source 75 irradiates light having a wavelength that is reflected or absorbed by the separator 40 to the bagged positive electrode 20.

The camera 80 is disposed above the bagged positive electrode 20. The camera 80 captures each component of the bagged positive electrode 20.

The control unit 160 detects a breakage in the separator 40 based on an image obtained by capturing the bagged positive electrode 20 with the camera 80. As a detection device or unit, the control unit 160 detects the portion in the image where two separators 40 are superposed, from the gray value of a black and white image obtained by capturing the bagged positive electrode 20 with the camera 80 (first portion in which light has transmitted two separators 40). In addition, as a determination device or unit, the control unit 160 determines a breakage of the separator 40 based on the distance between edges of the portion in the image where two separators 40 are superposed, and of the portion of the positive electrode 24 where light does not pass through. The gray value according to the present embodiment indicates the brightness of the black and white image.

The transmissive light source 70, the camera 80, and the control unit 160 configure the detection device according to the present embodiment.

Inspection Method of the Bagged Positive Electrode

Next, the inspection method of the bagged positive electrode 20 according to the first embodiment will be described next, with reference to FIG. 12. In the inspection method of the bagged positive electrode 20, positional correction of the bagged positive electrode 20, breakage detection of the separator 40, and the positional inspection of the separator 40 are carried out.

Figure 12:
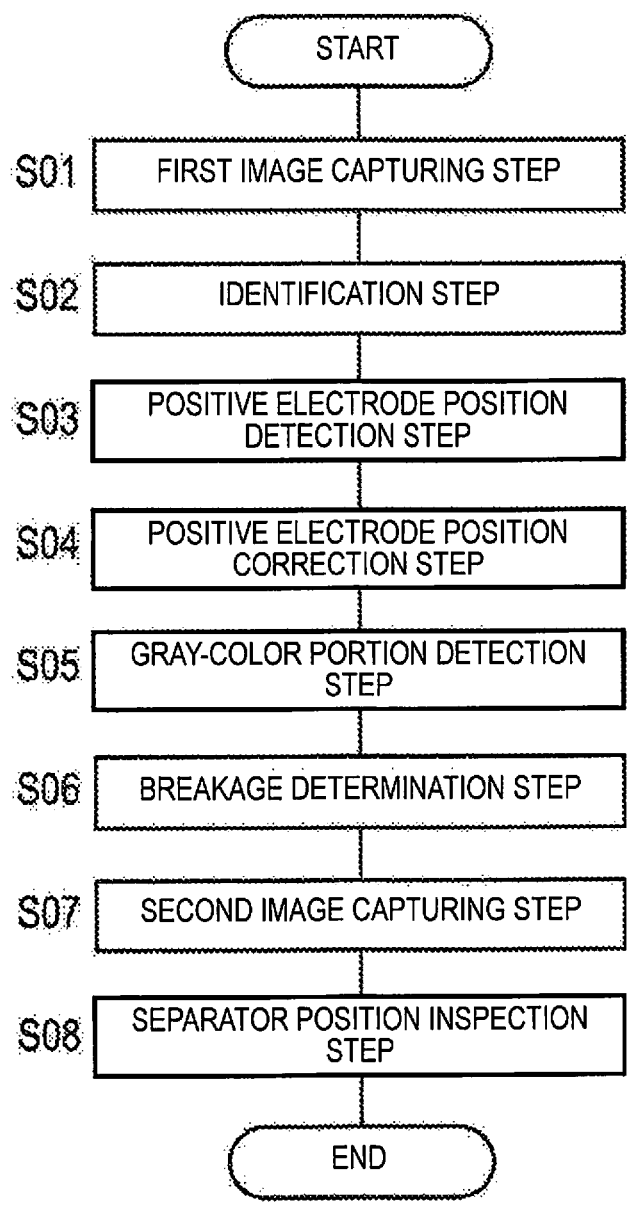
FIG. 12 is a flowchart illustrating a procedure of the inspection method of the bagged positive electrode according to the first embodiment.

FIG. 12 is a flowchart illustrating a procedure of the inspection method of the bagged positive electrode 20 according to the first embodiment.

Prior to starting the inspection of the bagged positive electrode 20, the intensity of the light that is irradiated from the transmissive light source 70 is adjusted (adjustment step). In the adjustment step, the intensity of light is adjusted so that light that is irradiated from the transmissive light source 70 and that has transmitted through two separators 40, and light that has transmitted through one separator 40, will have mutually different gray values according to the camera 80. Specifically, the intensity of light is adjusted by an adjustment dial. The control unit 160 may adjust the intensity of light as well.

Figure 13A:
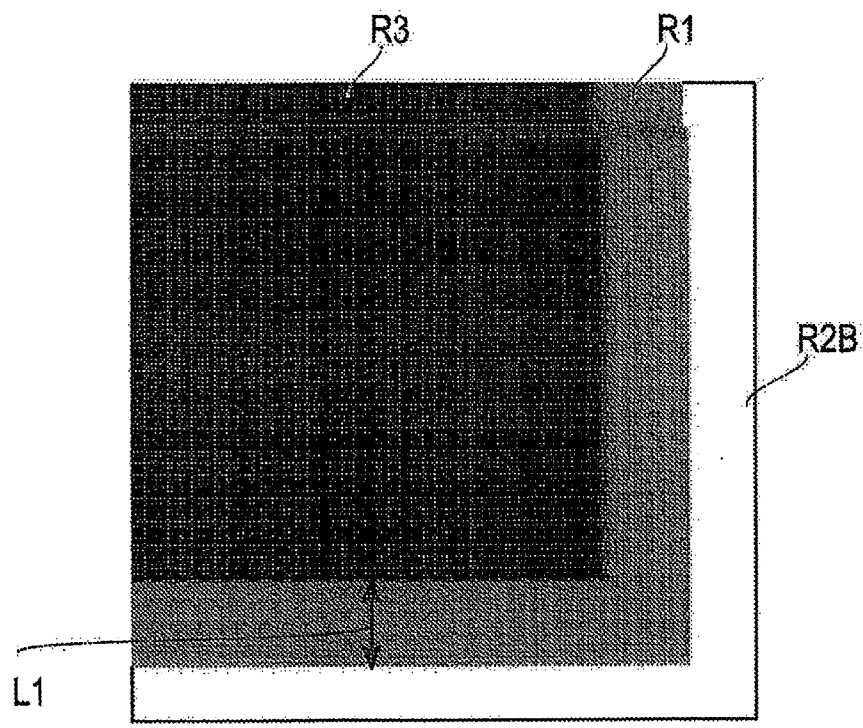
FIG. 13A is a view illustrating the captured image of a good bagged positive electrode in which the separator is not broken.
Figure 13B:
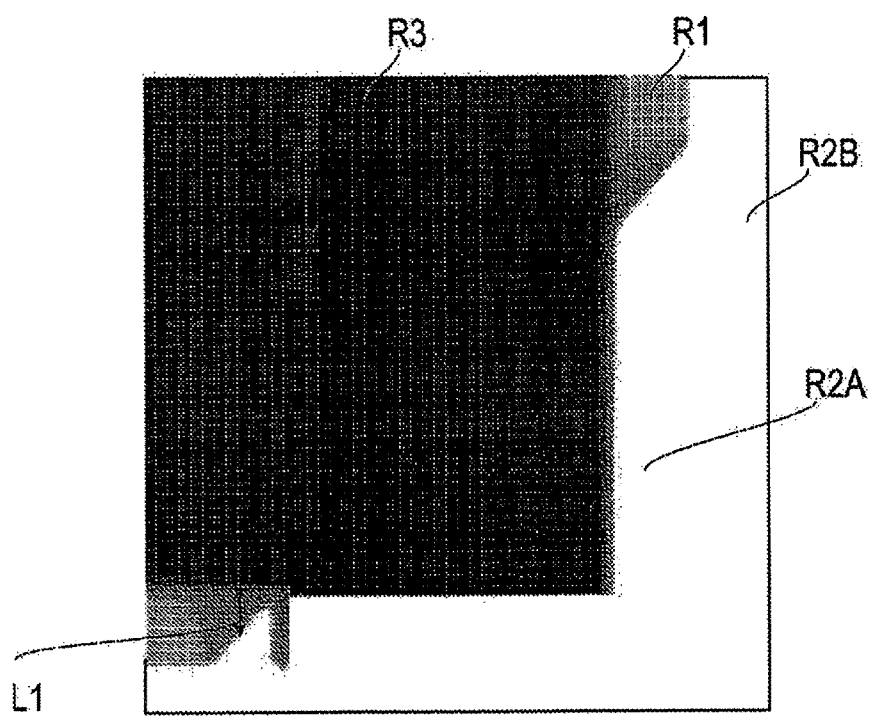
FIG. 13B is a view illustrating the captured image of a bagged positive electrode in which the separator is broken.

In a first image capturing step (image capturing step) S01, the control unit 160 irradiates light onto the bagged positive electrode 20 by the transmissive light source 70 while capturing the bagged positive electrode 20 with the camera 80. Images obtained by capturing the bagged positive electrode 20 with the camera 80 are illustrated in FIGS. 13A and 13B. FIG. 13A is a view illustrating the captured image of a good bagged positive electrode 20 in which the separator 40 is not broken; FIG. 13B is a view illustrating the captured image of a bagged positive electrode 20 in which the separator 40 is broken.

In FIGS. 13A and 13B, the black portion R3 corresponds to the portion where the positive electrode 24, which does not transmit light, is present. In addition, the gray-color portion R1 (for example, with a gray value of 220-230) that is present in around the black-color portion R3 corresponds to a portion where two sheets of separators 40 are superposes (first portion where light has transmitted through two separators 40). The white-color portions R2A, R2B which are present surrounding the gray-color portion R1 corresponds to a portion where there is only one sheet of the separator 40 (second portion where light has passed through one sheet of separator), or a portion where a bagged positive electrode 20 does not exist.

As described above, in the present embodiment, the intensity of light that is irradiated from the transmissive light source 70 is adjusted; therefore it is possible to distinguish between a gray-color portion R1 where two separators 40 are superposed, and a white-color portion R2A where there is only one separator.

In the identification Step S02, the control unit 160 identifies the outer perimeter end of the positive electrode 24 in the image obtained by capturing the bagged positive electrode 20 with a camera 80 in the image capturing step S01. Specifically, the control unit 160 applies image processing to the image obtained by capturing the bagged positive electrode 20 and removes the portion with a predetermined gray value or greater. By removing the portion with a predetermined gray value or greater, for example, the gray-color portion R1 where two sheets of separators 40 are superposed in FIG. 13 becomes white, and the black-color portion R3 where a positive electrode 24 is present will remain as is. As a result, the outer perimeter end of the positive electrode 24 can be identified from the border between the white color and black color.

In a positive electrode position detection Step S03, the control unit 160 detects the position of the positive electrode 24 based on the outer perimeter end of the positive electrode 24 identified in the identification Step S02. Specifically, in the image of FIG. 13, the black-color portion R3 where the positive electrode 24 is present is detected as the position of the positive electrode 24.

In a positive electrode position correction Step S04, the control unit 160 corrects the position of the positive electrode 24 (bagged positive electrode 20) with the XY stage 122. Specifically, the motors of the XY stage 122 are controlled so that the positive electrode 24 is disposed in a predetermined position, based on the position information of the positive electrode 24 that is detected in the positive electrode position detection Step S03. As a result, a bagged positive electrode 20 in which the position of the positive electrode 24 has been accurately positioned can be picked up every time.

As described above, in the first image capturing Step S01 to the positive electrode position correction Step S04, the control unit 160 detects the position of the positive electrode 24 and corrects the position of the bagged positive electrode 20.

In a gray-color portion detection step (detection step) S05, the control unit 160 detects a gray-color portion R1 where two sheets of separators 40 are superposed, from the gray values of the image obtained by capturing the bagged positive electrode 20 in the image capturing Step S01.

In a breakage determination step (determination step) S06, the control unit 160 determines a breakage of a separator 40 based on the distance L1 between edges of the gray-color portion R1 detected in the gray-color portion detection Step S05 and of the black-color portion R3 where a positive electrode 24 is present. The breakage determination Step S06 will be described in detail below, with reference to FIG. 13 again.

If FIGS. 13A and 13B are compared, in the case that the separator 40 is broken, there is a white-color portion R2A, where there is only one separator 40, around the black-color portion R3 where a positive electrode 24 is present. Accordingly, if the distance L1 between the edges of the periphery of the black-color portion R3 and of the gray-color portion R1 is equal to or greater than a predetermined distance (for example 0.5 Pixel in terms of the number of pixels of the camera 80) across the entire perimeter, it is determined that the separator 40 is not broken. On the other hand, if the distance L1 between the edges of the edges of the periphery of the black-color portion R3 and of the gray-color portion R1 is equal to or less than the predetermined distance in at least one location, it is determined that there is breakage in the separator 40.

As described above, in the gray-color portion detection Step S05 to the breakage determination Step S06, the control unit 160 detects a breakage in the separator 40.

In a second image capturing Step S07, the control unit 160 irradiates light onto the bagged positive electrode 20 by the reflected light source 75 from above, while capturing the bagged positive electrode 20 with the camera 80. An image obtained by capturing the bagged positive electrode 20 with the camera 80 is illustrated in FIG. 14.

Figure 14:
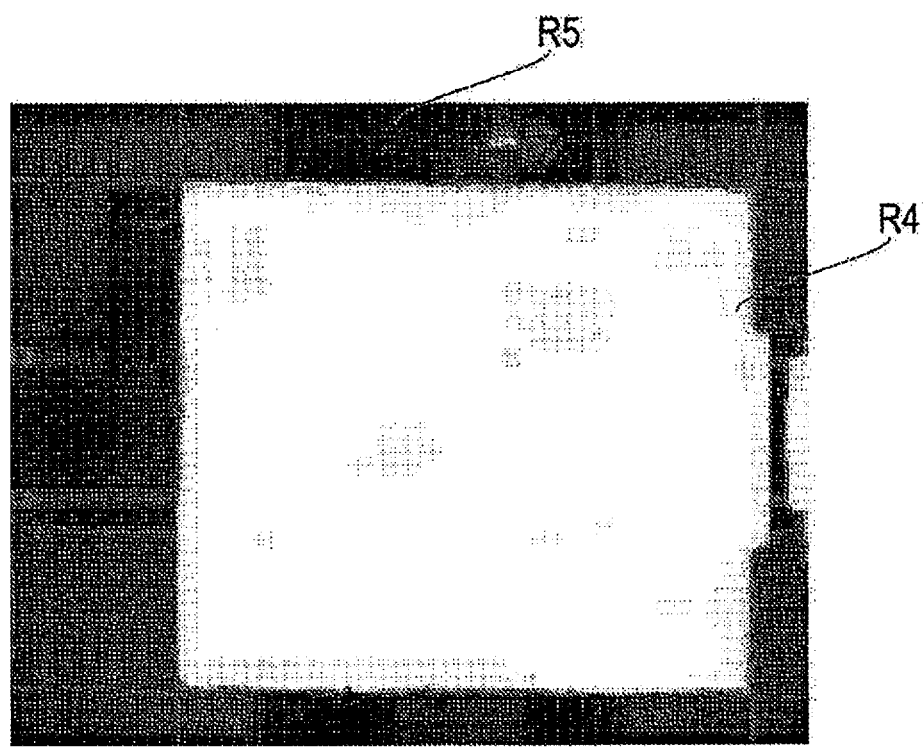
FIG. 14 is a view illustrating a captured image when capturing a bagged positive electrode with a camera, by irradiating light with a reflected light source.

In FIG. 14, the white-color portion R4 indicates the portion where a separator 40 is present. The black-color portion R5 that is present around the white-color portion R4 corresponds to the portion where a bagged positive electrode 20 is not present.

In a separator position inspection Step S08, the control unit 160 inspects the position of the separator 40, based on a captured image obtained in the second image capturing Step S07. Specifically, the white-color portion R4 illustrated in FIG. 14 is detected as the separator 40 portion, and the control unit 160 inspects the position of the detected separator 40 to determine whether or not the separator is disposed in a predetermined area.

As described above, in the second image capturing Step S07 to the separator position inspection Step S08, the control unit 160 inspects the position of the separator 40.

Figure 15:
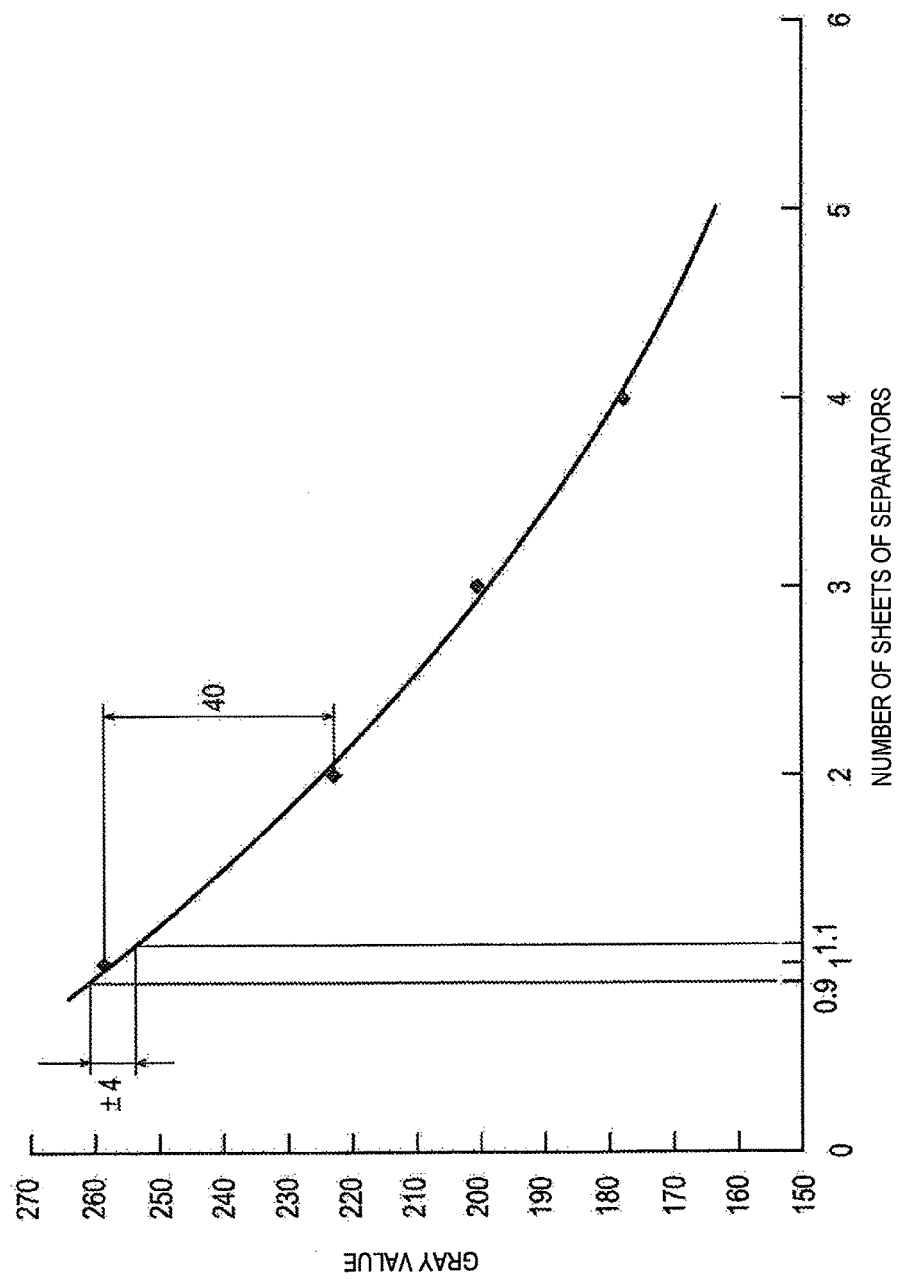
FIG. 15 is a graph illustrating the relationship between the gray value and the number of sheets of separators through which light is transmitted.

Next, how variation in the thickness of the separator 40 does not affect the detection of breakage of the separator 40 will be described, with reference to FIG. 15. FIG. 15 is a graph illustrating the relationship between the gray value and the number of sheets of separators 40 through which light is transmitted. In FIG. 15, the horizontal axis indicates the number of sheets of separators 40, and the vertical axis indicates the gray value. The color approaches white as the numerical value of the gray value increases, and approaches black as the numerical value decreases.

In general, there as about 10% of variation in the thickness of the separator 40. If this variation in thickness is converted to variation in the number of sheets based on one sheet of an ideal separator, the variation will be 0.9 to 1.1 sheets. Error in the gray value due to this variation in the number of sheets is ±4, as illustrated in FIG. 15. In contrast, the difference in the gray value for determining the number of sheets of separators 40 through which light is transmitted (for example one sheet, two sheets) is about 40. Therefore, variation in the gray value of ±4 is sufficiently small with respect to the difference in the gray value of about 40. Therefore, even if there is variation in the thickness of the separators 40, it is possible to distinguish between a gray-color portion R1 where two separators 40 are superposed, and a white-color portion R2A where there is only one separator 40.

In addition, when detecting the gray-color portion R1, even in a portion where two sheets of separators 40 are uniformly superposed, there are cases in which difference occurs in the gray values depending on the position within the image. In this case, the control unit 160 corrects the variation in the gray values (correction step).

Figure 16:
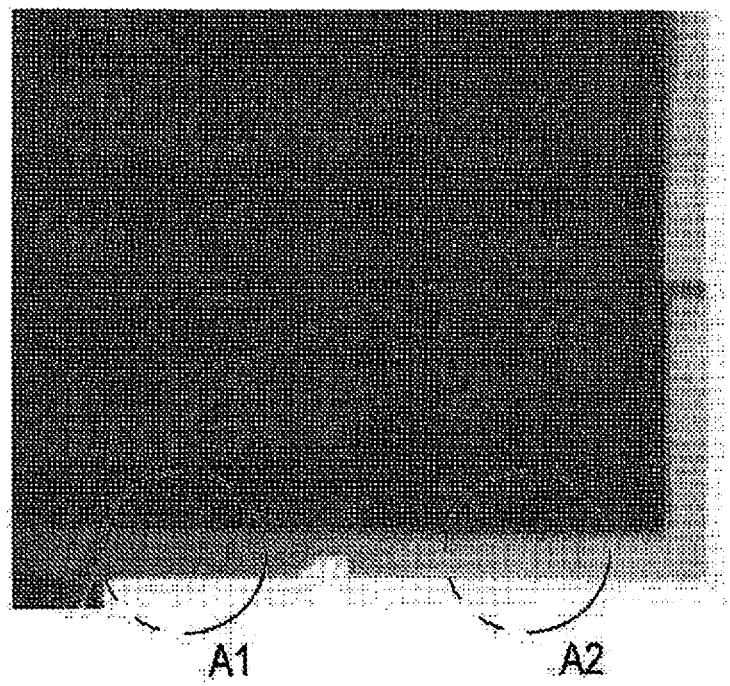
FIG. 16 is a view illustrating a captured image that contains uneven luminance.
Figure 17:
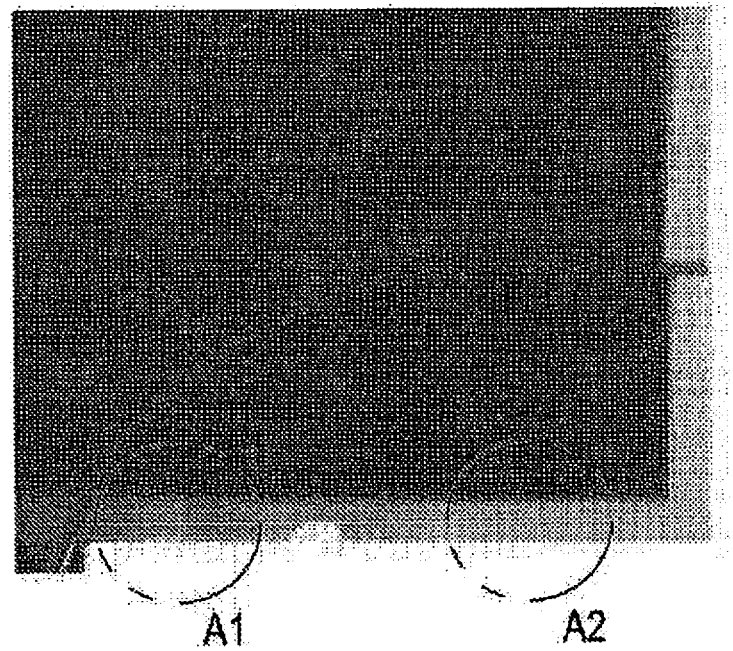
FIG. 17 is a view illustrating a captured image in which uneven luminance is reduced by a correction step.

The correction step will be described in detail with reference to FIG. 16 and FIG. 17. FIG. 16 is a view illustrating a captured image that contains uneven luminance. FIG. 17 is a view illustrating a captured image in which uneven luminance has been reduced by a correction step.

Prior to the correction step, the control unit 160 irradiates light with the transmissive light source 70 to the bagged positive electrode 20 comprising a separator 40 without breakage, and captures an image of the bagged positive electrode 20 with the camera 80. An image obtained by capturing the bagged positive electrode 20 with a camera 80 is illustrated in FIG. 16. In FIG. 16, it can be seen that differences in gray values are generated even when the number of sheets separators 40 that have been transmitted are the same (two sheets), in region A1 and region A2 indicated by the chain double-dashed lines. Luminance information including uneven luminance is obtained based on this image. This uneven luminance is caused by uneven luminance of the lighting, shadows of equipment such as the clamper 126, or the like.

Then, the control unit 160 reduces the uneven luminance included in the image obtained by capturing the bagged positive electrode 20 in the image capturing Step S01, based on the obtained luminance information. Specifically, by carrying out image processing with respect to locations with low gray values, the differences in the gray values with the locations with high gray values are made to be, for example, 10 or less. As a result, the differences in the gray values are reduced in region A1 and region A2, as illustrated in FIG. 17.

As described above, the detection method according to the present embodiment is a detection method in which light is irradiated on a bagged positive electrode 20, wherein a positive electrode 24 is disposed inside of a bag-shaped separator 40, to detect a breakage of the separator 40. The detection method comprises an image capturing Step S01, a gray-color portion detection Step S05, and a breakage determination Step S06. In the image capturing Step S01, light is irradiated on the bagged positive electrode 20 so that a gray-color portion R1 in which two layers of separators 40 are superposed and a white-color portion R2A which is only one layer of the separator 40, will have mutually different gray values, while capturing an image of the bagged positive electrode 20. In the gray-color portion detection Step S05, a gray-color portion R1 where two sheets of separators 40 are superposed is detected, from the gray values of the image obtained by capturing the bagged positive electrode 20 in the image capturing Step S01. In the breakage determination Step S06, a breakage of a separator 40 is determined based on the distance between edges of the gray-color portion R1 detected in the gray-color portion detection Step S05 and of the black-color portion R3 where a positive electrode 24 is present and light is not transmitted. Accordingly, it is possible to distinguish between a portion where the number of separators 40 is two sheets and a portion where the number of separators 40 is one sheet. Therefore, a breakage of a separator 40 can be detected regardless of the position of the separator 40, with respect to a bagged positive electrode 20, wherein positive electrode 24 is disposed inside of a bag-shaped separator 40.

In addition, an adjustment step is further provided before the image capturing step S01 for adjusting the intensity of light so that a gray-color portion R1 in which two layers of separators 40 are superposed and a white-color portion R2A which is only one layer of the separator 40, will have mutually different gray values. Accordingly, a gray-color portion R1 in which two layers of separators 40 are superposed and a white-color portion R2A which is only one layer of the separator 40 may be provided with mutually different gray values by a simple method.

In addition, in the adjustment step, the intensity of light is adjusted so that the color becomes white in the white-color portion R2A where there is only one separator 40, and the color becomes gray in the gray-color portion R1 where two separators 40 are superposed. Therefore, the detection of the gray-color portion R1 where two separators 40 are superposed in the gray-color portion detection Step S05 becomes easy.

Additionally, an identification Step S02 for identifying the outer perimeter end of the positive electrode 24 by removing the portion with a predetermined gray value or greater from the image obtained by capturing the bagged positive electrode 20 in the image capturing Step S01 is further provided between the image capturing Step S01 and the gray-color portion detection Step S05. Accordingly, not only can a breakage of the separator 40 be detected but also the position of the positive electrode 24 can be detected with a single capture; therefore, the manufacturing time can be shortened.

In addition, if there are regions in the image obtained by capturing the bagged positive electrode 20 in the image capturing Step S01, in which differences in the gray values always occur even if the number of separators 40 that have been passed through is the same, a correction step for correcting the differences in the gray values between said regions is also provided. Accordingly, differences in gray values caused by equipment shadows, uneven luminance of lighting, or the like are reduced, and breakage of a separator 40 can be more accurately detected.

In addition, according to the detection device of the present embodiment, when breakage has occurred in at least one separator 40 among the two separators 40 provided in a bagged positive electrode 20, said breakage can be detected.

Additionally, a positive electrode position detection Step S03 and a positive electrode position correction Step S04 are executed prior to the gray-color portion detection Step S05 after the capturing in the first image capturing Step S01. Therefore, the position of the positive electrode 24 can be quickly corrected to prepare for the pick-up of the bagged positive electrode 20 by the L-shaped arm 112. Therefore, the gray-color portion detection Step S05 can be executed without delaying the pick-up operation by the L-shaped arm 112. For example, the gray-color portion detection Step S05 may take place in parallel with the pick-up operation by the L-shaped arm 112. In this manner, by executing Steps S03, S04 which are directly related to the lamination operation before Step S05 which is not directly related, the lamination speed of the bagged positive electrode 20 and the negative electrode 30 can be increased.

Second Embodiment

Next, the second embodiment of the present invention will be described. Descriptions of portions shared with the first embodiment will be omitted, and portions characteristic to only the second embodiment will be described. The inspection method of the bagged positive electrode 20 according to the second embodiment differs from the inspection method according to the first embodiment in the point that image capturing by the camera 80 is carried out three times. The configuration of the lithium ion secondary battery 10 and the configuration of the sheet laminating device 100 are the same as in the first embodiment, and thus the descriptions thereof are omitted.

The inspection method of the bagged positive electrode 20 according to the second embodiment will be described below, with reference to FIG. 18.

Figure 18:
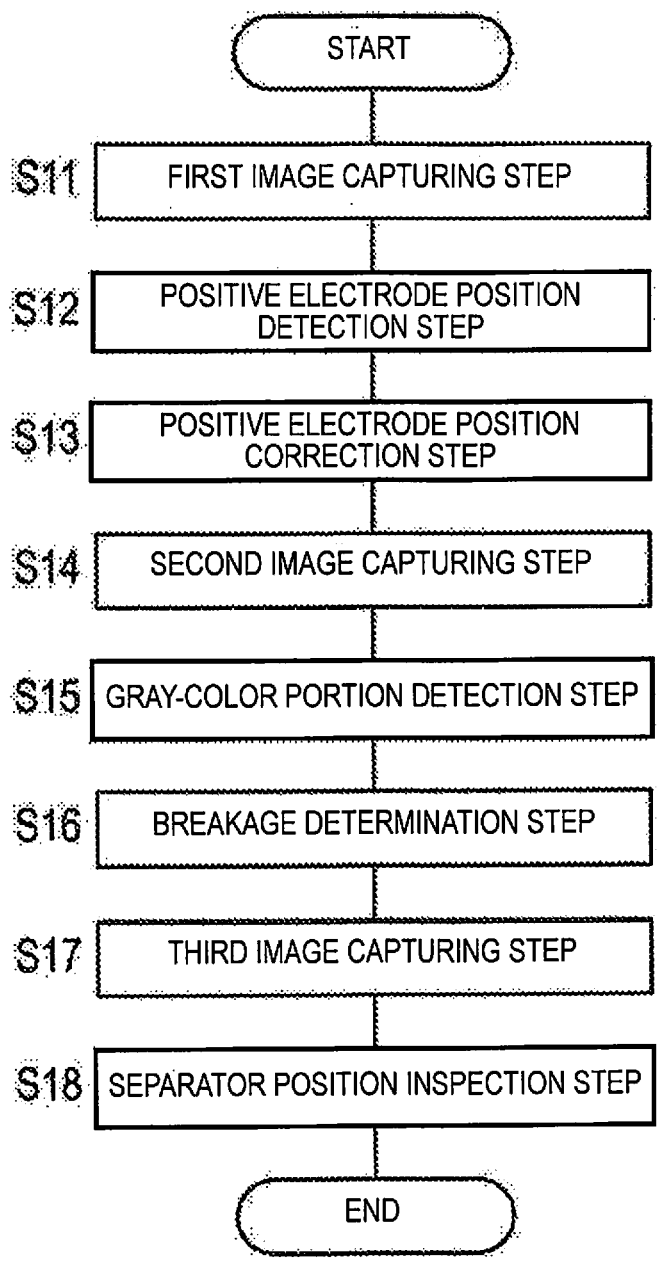
FIG. 18 is a flowchart illustrating a procedure of the inspection method of the bagged positive electrode according to the second embodiment.

FIG. 18 is a flowchart illustrating a procedure of the inspection method of the bagged positive electrode 20 according to the second embodiment.

In a first image capturing Step S11, the control unit 160 adjusts the intensity of the light that is irradiated from the transmissive light source 70 so that the portion where a positive electrode 24 is present and light is not transmitted through becomes black and the portion where a separator 40 is present becomes white regardless of the number of sheets. After adjusting the intensity of light, the control unit 160 captures and image of the bagged positive electrode 20 while irradiating light on the bagged positive electrode 20.

In a positive electrode position detection Step S12, the control unit 160 detects the position of the positive electrode 24 based on an image obtained by capturing the bagged positive electrode 20 in the first image capturing Step S11. Specifically, the black-color portion in the captured image is detected as the position of the positive electrode 24.

In a positive electrode position correction Step S13, the control unit 160 corrects the position of the positive electrode 24 (bagged positive electrode 20) with the XY stage 122. The specific correction method is the same as the positive electrode position correction Step S04 of the first embodiment; thus the description thereof is omitted.

As described above, in the first image capturing Step S11 to the positive electrode position correction Step S13, the control unit 160 detects the position of the positive electrode 24 and corrects the position of the bagged positive electrode 20.

In a second image capturing step (image capturing step) S14, the control unit 160 irradiates light on the bagged positive electrode 20 so that a gray-color portion R1 in which two layers of separators 40 are superposed and a white-color portion R2A which is only one layer of the separator 40, will have mutually different gray values, while capturing an image. At this time, an image that is the same as in the image capturing Step S01 according to the first embodiment (refer to FIG. 13) is captured.

In a gray-color portion detection step (detection step) S15, the control unit 160 detects a gray-color portion R1 where two sheets of separators 40 are superposed, from the gray values of the image obtained by capturing the bagged positive electrode 20 in the second image capturing Step S14. The specific detection method is the same as the gray-color portion detection Step S05 of the first embodiment; thus the description thereof is omitted.

In a breakage determination step (determination step) S16, the control unit 160 determines a breakage of a separator 40 based on the distance between edges of the gray-color portion R1 detected in the gray-color portion detection Step S15 and of the black-color portion R3 where a positive electrode 24 is present and light is not transmitted. The specific determination method is the same as the breakage determination Step S06 of the first embodiment; thus the description thereof is omitted.

As described above, in the second image capturing Step S14 to the breakage determination Step S16, the control unit 160 detects breakage in the separator 40.

In a third image capturing Step S17, the control unit 160 irradiates light onto the bagged positive electrode 20 by the reflected light source 75 from above, while capturing the bagged positive electrode 20 with the camera 80. At this time, an image that is the same as in the second image capturing Step S07 according to the first embodiment is captured.

In a separator position inspection Step S18, the control unit 160 detects the position of the separator 40, based on a captured image obtained in the third image capturing Step S17. The specific detection method is the same as the separator position detection method S08 of the first embodiment; thus the description thereof is omitted.

As described above, in the third image capturing Step S17 to the separator position inspection Step S18, the control unit 160 inspects the position of the separator 40.

In the second embodiment, compared to the first embodiment, a first image capturing Step S11 is added. The intensity of the light that is irradiated in the first image capturing Step S11 is greater than the intensity of light that is irradiated in the first image capturing Step S01 of the first embodiment. Accordingly, a black-color portion R3 where a positive electrode 24 exists and light is not passed through can be easily detected without executing the identification Step S02 of the first embodiment.

A modified example of the above-described embodiment will be described below.

Modified Example

In the first and second embodiments described above, a method to detect breakage in the two separators 40 which are provided in one bagged positive electrode 20 was described. However, the invention is not limited thereto; breakage of separators 40 in a laminated body in which multiple bagged positive electrodes 20 and negative electrodes 30 are laminated may be detected. An example of when the number of sheets of separator 40 in the laminated body is n will be described. At this time, in the image capturing step, it is sufficient to irradiate light on the bagged positive electrode 20 (laminated body) so that a portion in which n layers of separators 40 are superposed and a portion in which there are n−1 layers of separators, will have mutually different gray values, while capturing an image of the bagged positive electrode 20 (laminated body). Breakage in separators 40 in a laminated body can thereby be detected.

In addition, in the above-described embodiment, a bagged positive electrode 20 is formed by a positive electrode 24 being disposed inside of a bag-shaped separator 40 shaped. However, the invention is not limited thereto; a bagged negative electrode may formed by a negative electrode 30 being disposed inside of a bag-shaped separator 40. In this case, breakage of separators in a bagged negative electrode will be detected.

In addition, in the above-described embodiments, the intensity of light that is irradiated from the transmissive light source 70 is adjusted so that a gray-color portion R1 where two separators 40 are superposed, and a white-color portion R2A where there is only one separator 40 will have mutually different gray values. However, the invention is not limited thereto; a gray-color portion R1 where two separators 40 are superposed, and a white-color portion R2A where there is only one separator 40 may be configured to have mutually different gray values by adjusting the shutter speed of the camera 80.

In addition, in the above-described embodiment, the light of the transmissive light source 70 was adjusted so that the white-color portion R2A where there is only one sheet of the separator 40 will indicate a white color. However, the light of the transmissive light source 70 may be adjusted so that the gray-color portion R1 in which two layers of separators 40 are superposed indicates a dark gray color and the white-color portion R2A which is only one layer of the separator 40 indicates a light gray color.

Further, in the above-described embodiment, a breakage in the separator 40 was determined using gray values in a black and white image. However, breakage of the separator 40 may be determined using a captured image in color. When using a color captured image, breakage of a separator 40 can be determined by using the brightness of the captured image. In addition, a breakage in the separator 40 may be determined by converting the color captured image to a black and white image and using the gray values therein.

The invention claimed is:

1. A detection method for detecting breakage of a bag-shaped separator surrounding an electrode such that the electrode is disposed inside the bag-shaped separator, the method comprising:
    irradiating light onto the bag-shaped separator so that a first portion, in which the light has been transmitted through n layers of the bag-shaped separator, and a second portion, in which the light has been transmitted through equal to or less than n−1 layers of the bag-shaped separator, will have mutually different brightness levels, while capturing an image of the electrode disposed inside the bag-shaped separator; wherein n is an integer greater than 1; and;
    detecting the first portion from the brightness of the captured image of the electrode; and
    determining a breakage of the bag-shaped separator, based on the distance between edges of the first portion, and of an electrode portion where the light does not pass through.

2. The detection method according to claim 1, further comprising
    adjusting an intensity of the light before capturing the image, so that the first portion and the second portion have mutually different brightness levels.

3. The detection method according to claim 2, wherein
    the adjusting the intensity of the light includes adjusting the intensity of the light so that the brightness in the second portion has a same value as a brightness of a region outside of the bag-shaped separator, and so that the brightness in the first portion has a lower value than the brightness of the region outside of the bag-shaped separator.

4. The detection method according to claim 3, further comprising
    identifying an outer perimeter end of the electrode by removing a portion with a predetermined brightness or more from the image obtained by capturing the electrode when capturing the image, between capturing the image and the detecting the first portion.

5. The detection method according to claim 3, further comprising
    correcting differences in brightness in regions, in which differences in the brightness are the same, even when a plurality of bag-shaped separators have been passed through.

6. The detection method according to claim 2, further comprising
    identifying an outer perimeter end of the electrode by removing a portion with a predetermined brightness or more from the image obtained by capturing the electrode when capturing the image, between capturing the image and the detecting the first portion.

7. The detection method according to claim 2, further comprising
    correcting differences in brightness in regions, in which differences in the brightness are the same, even when a plurality of bag-shaped separators have been passed through.

8. The detection method according to claim 1, further comprising
    identifying an outer perimeter end of the electrode by removing a portion with a predetermined brightness or more from the image obtained by capturing the electrode when capturing the image, between capturing the image and the detecting the first portion.

9. The detection method according to claim 8, further comprising
    correcting differences in brightness in regions, in which differences in the brightness are the same, even when a plurality of bag-shaped separators have been passed through.

10. The detection method according to claim 1, further comprising
    correcting differences in brightness in regions, in which differences in the brightness are the same, even when a plurality of bag-shaped separators have been passed through.

11. A detection device configured to irradiate light on a bag-shaped separator surrounding an electrode such that the electrode is disposed inside the bag-shaped separator to detect breakage of the bag-shaped separator, the detection device comprising:

an image capturing device configured to irradiate the light onto the bag-shaped separator by an irradiation device so that a first portion, in which the light has been transmitted through n-layers of the bag-shaped separator, and a second portion in which the light has been transmitted through equal to or less than n−1 layers of the bag-shaped separator, have mutually different brightness levels, while capturing an image of the electrode disposed inside the bag-shaped separator; wherein n is an integer greater than 1; and;

a detection device configured to detect the first portion from the brightness of the image that is obtained by capturing the electrode by the image capturing device, and a determination device configured to determine breakage of the bag-shaped separator, based on a distance between edges of the first portion which is detected by the detection device, and of an electrode portion where the light does not pass through.

* * * * *